United States Patent
Blinn et al.

(10) Patent No.: US 9,226,998 B2
(45) Date of Patent: Jan. 5, 2016

(54) METHOD OF MANUFACTURING A DRUG DELIVERY SYSTEM USING GAS CLUSTER ION BEAM IRRADIATION

(75) Inventors: Stephen M. Blinn, Amherst, NH (US); Richard C. Svrluga, Newton, MA (US)

(73) Assignee: Exogenesis Corporation, Billerica, MA (US)

( * ) Notice: Subject to any disclaimer, the term of this patent is extended or adjusted under 35 U.S.C. 154(b) by 509 days.

(21) Appl. No.: 13/596,236

(22) Filed: Aug. 28, 2012

(65) Prior Publication Data

US 2012/0321707 A1 Dec. 20, 2012

Related U.S. Application Data

(60) Continuation of application No. 13/041,525, filed on Mar. 7, 2011, now Pat. No. 8,252,418, which is a division of application No. 11/550,069, filed on Oct. 17, 2006, now Pat. No. 7,923,055, which is a continuation-in-part of application No. 11/349,483, filed on Feb. 7, 2006, now Pat. No. 7,666,462, which is a continuation-in-part of application No. 10/144,919, filed on May 13, 2002, now Pat. No. 7,105,199.

(60) Provisional application No. 60/290,389, filed on May 11, 2001, provisional application No. 60/317,652, filed on Sep. 6, 2001.

(51) Int. Cl.
| | |
|---|---|
| *A61L 33/00* | (2006.01) |
| *B05D 3/00* | (2006.01) |
| *C23C 14/00* | (2006.01) |
| *A61L 31/16* | (2006.01) |
| *A61F 2/82* | (2013.01) |
| *C23C 14/02* | (2006.01) |
| *C23C 14/22* | (2006.01) |
| *C23C 14/50* | (2006.01) |

(52) U.S. Cl.
CPC . *A61L 31/16* (2013.01); *A61F 2/82* (2013.01); *C23C 14/022* (2013.01); *C23C 14/221* (2013.01); *C23C 14/505* (2013.01); *A61F 2250/0067* (2013.01); *A61L 2300/406* (2013.01); *A61L 2300/416* (2013.01); *A61L 2300/42* (2013.01); *A61L 2300/426* (2013.01); *A61L 2300/61* (2013.01); *A61L 2300/62* (2013.01); *A61L 2400/18* (2013.01); *H01J 2237/0812* (2013.01); *Y10T 428/249988* (2015.04); *Y10T 428/31504* (2015.04)

(58) Field of Classification Search
CPC ........... A61L 33/00; B05D 3/00; C23C 14/00
See application file for complete search history.

(56) References Cited

U.S. PATENT DOCUMENTS

| | | | | |
|---|---|---|---|---|
| 3,710,795 | A | | 1/1973 | Higuchi et al. |
| 3,854,480 | A | * | 12/1974 | Zaffaroni ................ 424/424 |
| 4,851,231 | A | * | 7/1989 | Urquhart et al. ............ 424/469 |
| 4,986,006 | A | | 1/1991 | Weaver |
| 5,123,924 | A | | 6/1992 | Sioshansi et al. |
| 5,133,757 | A | | 7/1992 | Sioshansi et al. |
| 5,302,397 | A | * | 4/1994 | Amsden et al. ............ 424/473 |
| 5,419,760 | A | | 5/1995 | Narciso |
| 5,459,326 | A | | 10/1995 | Yamada |
| 5,707,684 | A | | 1/1998 | Hayes et al. |
| 5,763,504 | A | | 6/1998 | Matsuda et al. |
| 5,814,194 | A | | 9/1998 | Deguchi et al. |
| 5,837,313 | A | | 11/1998 | Ding et al. |
| 5,843,172 | A | | 12/1998 | Yan |
| 5,885,616 | A | * | 3/1999 | Hsiao et al. ............ 424/472 |
| 6,120,847 | A | | 9/2000 | Yang et al. |
| 6,143,354 | A | | 11/2000 | Koulik et al. |
| 6,153,252 | A | * | 11/2000 | Hossainy et al. ............ 427/2.3 |
| 6,156,373 | A | | 12/2000 | Zhong et al. |
| 6,207,282 | B1 | | 3/2001 | Deguchi et al. |
| 6,331,227 | B1 | | 12/2001 | Dykstra et al. |
| 6,416,820 | B1 | * | 7/2002 | Yamada et al. ............ 427/530 |
| 6,451,871 | B1 | | 9/2002 | Winterton et al. |
| 6,486,478 | B1 | | 11/2002 | Libby et al. |
| 6,491,800 | B2 | | 12/2002 | Kirkpatrick et al. |
| 6,635,082 | B1 | | 10/2003 | Hossainy et al. |
| 6,641,607 | B1 | | 11/2003 | Hossainy et al. |
| 6,676,989 | B2 | | 1/2004 | Kirkpatrick et al. |
| 6,716,444 | B1 | | 4/2004 | Castro et al. |
| 6,746,773 | B2 | | 6/2004 | Llanos et al. |

(Continued)

FOREIGN PATENT DOCUMENTS

| | | |
|---|---|---|
| JP | 10-66721 A | 10/1998 |
| WO | 2007092894 A2 | 8/2007 |
| WO | 2009036373 A2 | 3/2009 |

OTHER PUBLICATIONS

International Search Report for PCT/US07/61787 dated Apr. 24, 2006.

(Continued)

*Primary Examiner* — Bret Chen
(74) *Attorney, Agent, or Firm* — Burns & Levinson LLP; Jerry Cohen; David W. Gomes

(57) ABSTRACT

A method for producing a drug delivery system provides a member including a combination of a drug substance and a polymer or other material; and forms a layer on a surface of the combination using gas cluster ion beam irradiation, which layer determines a release rate for the drug substance, wherein the layer is an encapsulating layer formed by densifying or carbonizing components of the drug or of the polymer or of the other material by the gas cluster ion beam irradiation.

4 Claims, 5 Drawing Sheets

(56) References Cited

U.S. PATENT DOCUMENTS

| | | |
|---|---|---|
| 6,764,505 B1 | 7/2004 | Hossainy et al. |
| 6,805,898 B1 | 10/2004 | Wu et al. |
| 6,863,786 B2 | 3/2005 | Blinn et al. |
| 6,984,404 B1 | 1/2006 | Talton et al. |
| 7,105,199 B2 | 9/2006 | Blinn et al. |
| 7,431,959 B1 | 10/2008 | Dehnad |
| 7,666,462 B2 | 2/2010 | Blinn et al. |
| 2002/0017454 A1 | 2/2002 | Kirkpatrick |
| 2002/0139961 A1 | 10/2002 | Kinoshita et al. |
| 2002/0188324 A1 | 12/2002 | Blinn et al. |
| 2003/0009233 A1 | 1/2003 | Blinn et al. |
| 2003/0143315 A1 | 7/2003 | Pui et al. |
| 2005/0025804 A1 | 2/2005 | Heller |
| 2005/0043787 A1 | 2/2005 | Kutryk et al. |
| 2005/0244453 A1 | 11/2005 | Stucke et al. |
| 2007/0087034 A1 | 4/2007 | Blinn et al. |
| 2009/0036373 A1 | 2/2009 | Lang |
| 2009/0074834 A1 | 3/2009 | Kirkpatrick et al. |
| 2009/0098186 A1 | 4/2009 | Kirkpatrick et al. |
| 2010/0098833 A1 | 4/2010 | Blinn et al. |

OTHER PUBLICATIONS

Fehsenfeld P. et al., Production of Radioactive Stents:, Nachrichten Forschungszentrum Karlsruhe, 2000, pp. 81-86, vol. 32-1, Germany.

International Preliminary Report on Patentability for PCT/US07/61787 dated Aug. 21, 2003.

Matsuo, J. et al, What size of cluster is most appropreate for SIMS? Applied Surface Science 255 (2008) pp. 1235-1238.

Translation of JP 10-66721.

* cited by examiner

METHOD OF MANUFACTURING A DRUG DELIVERY SYSTEM USING GAS CLUSTER ION BEAM IRRADIATION

CROSS-REFERENCE TO RELATED APPLICATIONS

This application is a continuation of U.S. patent application Ser. No. 13/041,525, filed Mar. 7, 2011, now U.S. Pat. No. 8,252,418 entitled "Drug Delivery System and Method of Manufacturing Thereof," which in turn is a divisional of U.S. patent application Ser. No. 11/550,069 filed Oct. 17, 2006, now U.S. Pat. No. 7,923,055 entitled "Drug Delivery System and Method of Manufacturing Thereof," which in turn is a continuation-in-part application of U.S. patent application Ser. No. 11/349,483 entitled "Drug Delivery System and Method of Manufacturing Thereof", filed Feb. 7, 2006, now U.S. Pat. No. 7,666,462 which in turn is a continuation-in-part of U.S. patent application Ser. No. 10/144,919 entitled "Method and System for Improving the Effectiveness of Medical Devices by Adhering Drugs to the Surface Thereof", filed 13 May 2002, issued as U.S. Pat. No. 7,105,199, which claims the benefit of priority of U.S. provisional application Ser. Nos. 60/290,389 filed May 11, 2001, and 60/317,652 filed Sep. 6, 2001, each entitled "Method and System for Improving the Effectiveness of Medical Devices by Applying/Adhering Drugs to their Surface in Combination with the Application of Ion Beam Technology", and each being incorporated herein by reference in their entirety for all purposes.

FIELD OF THE INVENTION

This invention relates generally to drug delivery systems such as, for example, medical devices implantable in a mammal (e.g., coronary stents, prostheses, etc.), and more specifically to a system and method for controlling the surface characteristics of such drug delivery systems such as, for example, the drug release rate and bio-reactivity.

BACKGROUND OF THE INVENTION

A coronary stent is an implantable medical device that is used in combination with balloon angioplasty. Balloon angioplasty is a procedure used to treat coronary atherosclerosis. Balloon angioplasty compresses built-up plaque against the walls of the blocked artery by the inflation of a balloon at the tip of a catheter inserted into the artery during the angioplasty procedure. Unfortunately, the body's response to this procedure often includes thrombosis or blood clotting and the formation of scar tissue or other trauma-induced tissue reactions at the treatment site. Statistics show that restenosis or re-narrowing of the artery by scar tissue after balloon angioplasty occurs in up to 35 percent of the treated patients within only six months after these procedures, leading to severe complications in many patients.

To reduce restenosis, cardiologists are now often placing small tubular devices of various forms, such as wire mesh; expandable metal; and non-degradable and biodegradable polymers called a coronary stent at the site of blockage during balloon angioplasty. The goal is to have the stent act as a scaffold to keep the coronary artery open after the removal of the balloon.

However, there are also serious complications associated with the use of coronary stents. Coronary restenotic complications associated with stents occur in 16 to 22 percent of all cases within six months after insertion of the stent and are believed to be caused by many factors acting alone or in combination. These complications could be reduced by several types of drugs introduced locally at the site of stent implantation. Because of the substantial financial costs associated with treating the complications of restenosis, such as catheterization, restenting, intensive care, etc., a reduction in restenosis rates would save money and reduce patient suffering.

Numerous studies suggest that the current popular designs of coronary stents are functionally equivalent. Although the use of coronary stents is growing, the benefits of their use remain controversial in certain clinical situations or indications due to their potential complications. It is widely held that during the process of expanding the stent, damage occurs to the endothelial lining of the blood vessel triggering a healing response that re-occludes the artery. To help combat that phenomenon, drug-coated stents are being introduced to the market to help control the abnormal cell growth associated with this healing response. These drugs are typically mixed with a liquid polymer and applied to the stent surface, The polymer coating can include several layers such as the above drug containing layer as well as a drug free encapsulating layer, which can help to reduce the initial drug release amount caused by initial exposure to liquids when the device is first implanted. A further base coating of polymer located beneath the drug bearing layer is also known. One example of this arrangement used on stainless steel stents includes a base layer of Paralene C. and a drug/polymer mixture including polyethylene-co-vinyl acetate (PEVA) and poly n-butyl methacrylate (PBMA) in a two to one ratio, along with an non-drug impregnated top layer of the same mixture of PEVA and PBMA. The drug used is Sirolirnus, a relatively new immunosuppressant drug also known as Rapamycin. Several other drug/polymer combinations exist from several manufactures.

In view of this new approach to in situ drug delivery, it is desirable to have greater control over the drug release rate from the implantable device as well as control over other surface characteristics of the drug delivery medium.

It is therefore an object of this invention to provide a means of controlling surface characteristics of a drug eluting material using gas cluster ion beam technology.

It is a further object of this invention to improve the functional characteristics of known in situ drug release mechanisms using gas cluster ion beam technology.

SUMMARY OF THE INVENTION

The objects set forth above as well as further and other objects and advantages of the present invention are achieved by the invention described herein below.

In one embodiment, a drug delivery system, comprises a member including a combination of a drug substance and a polymer or other material, and an encapsulating layer formed in an outer surface of the member by gas cluster ion beam irradiation of the outer surface of the member, which encapsulating layer is adapted to determine a release rate for the drug from the member.

The encapsulating layer may include a plurality of openings located at an outer surface of the encapsulating layer and adapted to permit amounts of the drug substance to be released from the member at a rate determined by the encapsulating layer. The encapsulating layer may include a carbonized or densified matrix. The encapsulating layer may be adapted to improve a measure of biocompatibility of the member.

The member may be located on a surface of a medical device. The drug substance may be selected from the group consisting of anti-coagulants, antibiotics, anti-tumor substances, immune-suppressing agents, vasodilators, anti-prolifics, anti-thrombotic substances, anti-platelet substances, cholesterol reducing agents and combinations thereof.

A medical device may include the drug delivery system described above.

In another embodiment, a drug delivery system comprises a cohesive mixture including a combination of a drug substance and a polymer or other material, and a carbonized or densified matrix formed on an outer surface of the cohesive mixture, which carbonized or densified matrix is adapted to determine a release rate for the drug substance from the cohesive mixture.

In yet another embodiment, a method for producing a drug delivery system, comprises the steps of providing a member including a combination of a drug substance and a polymer or other material, and irradiating an outer surface of the member with a gas cluster ion beam to determine a release rate for the drug substance from the member.

The step of providing a member may include forming a cohesive mixture of the drug substance and the polymer or other material on a surface of a medical device. The step of irradiating may include forming an encapsulating layer on at least an external surface of the member, which encapsulating layer is adapted to control release of the drug substance from the member. The encapsulating layer may include a plurality of openings at an outer surface of the encapsulating layer so as to permit portions of the drug substance to be released from the member at a rate determined by the encapsulating layer. The encapsulating layer may include a carbonized or densified matrix.

The step of providing a member may include the steps of providing a polymer element and adhering a drug substance to an outer surface of the polymer element. The step of providing a polymer element may include the step of irradiating the outer surface of the polymer element with a gas cluster ion beam prior to the step of adhering. The step of irradiating may be adapted to lower in situ chemical reactivity of the external surface of the cohesive mixture. The drug substance may be selected from the group consisting of anti-coagulants, antibiotics, anti-tumor substances, immune-suppressing agents, vasodilators, anti-prolifics, anti-thrombotic substances, anti-platelet substances, cholesterol reducing agents and combinations thereof.

BRIEF DESCRIPTION OF THE DRAWINGS

For a better understanding of the present invention, together with other and further objects thereof, reference is made to the accompanying drawings, wherein.

DETAILED DESCRIPTION OF THE DRAWINGS

Figure 1:
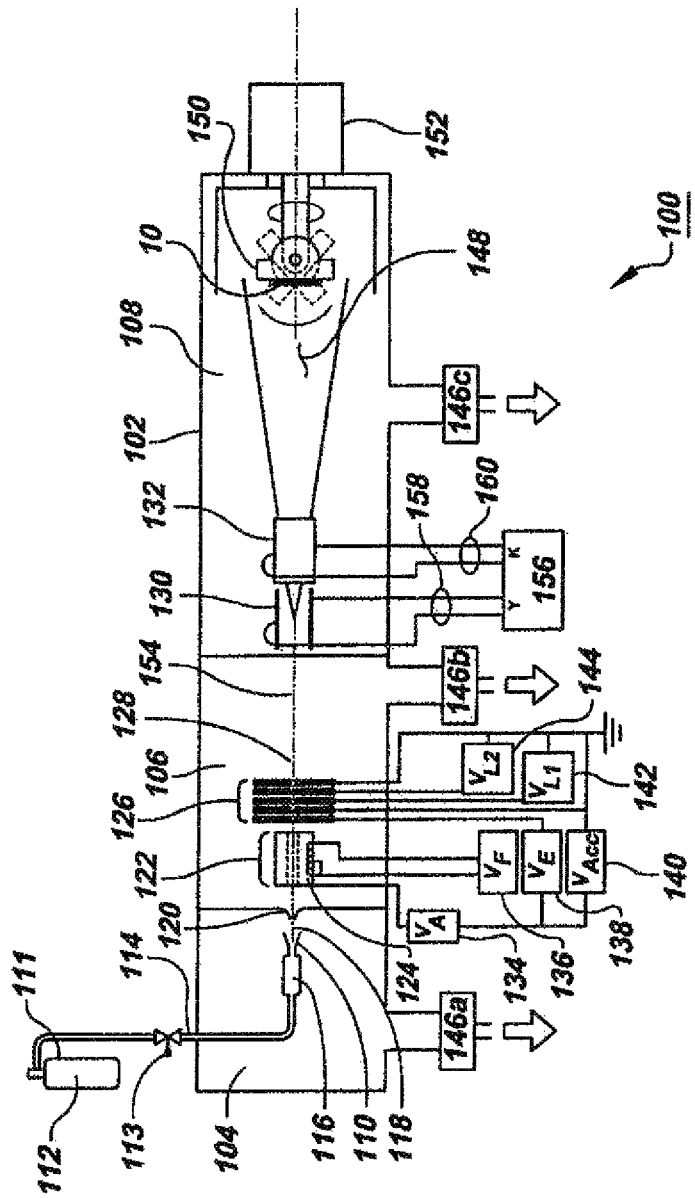
FIG. 1 is a schematic view of a gas cluster ion beam processing system used for practicing the method of the present invention.

Beams of energetic ions, electrically charged atoms or molecules accelerated through high voltages under vacuum, are widely utilized to form semiconductor device junctions, to smooth surfaces by sputtering, and to enhance the properties of semiconductor thin films. hi the present invention, these same beams of energetic ions are utilized for affecting surface characteristics of drug eluting medical devices, such as, for example, coronary stents, thereby enhancing the drug delivery properties and the bio-compatibility of such drug delivery systems.

In the preferred embodiment of the present invention, gas cluster ion beam GCIB processing is utilized. Gas cluster ions are formed from large numbers of weakly bound atoms or molecules sharing common electrical charges and accelerated together through high voltages to have high total energies. Cluster ions disintegrate upon impact and the total energy of the cluster is shared among the constituent atoms. Because of this energy sharing, the atoms are individually much less energetic than the case of conventional ions or ions not clustered together and, as a result, the atoms penetrate to much shorter depths. Surface sputtering effects are orders of magnitude stronger than corresponding effects produced by conventional ions, thereby making important microscale surface effects possible that are not possible in any other way.

The concept of GCIB processing has only emerged over the past decade. Using a GCIB for dry etching, cleaning, and smoothing of materials is known in the art and has been described, for example, by Deguchi, et al, in U.S. Pat. No. 5,814,194, "Substrate Surface Treatment Method", 1998. Because ionized clusters containing on the order of thousands of gas atoms or molecules may be formed and accelerated to modest energies on the order of a few thousands of electron volts, individual atoms or molecules in the clusters may each only have an average energy on the order of a few electron volts. It is known from the teachings of Yamada in, for example, U.S. Pat. No. 5,459,326, that such individual atoms are not energetic enough to significantly penetrate a surface to cause the residual sub-surface damage typically associated with plasma polishing. Nevertheless, the clusters themselves are sufficiently energetic (some thousands of electron volts) to effectively etch, smooth, or clean hard surfaces.

Because the energies of individual atoms within a gas cluster ion are very small, typically a few eV, the atoms penetrate through only a few atomic layers, at most, of a target surface during impact. This shallow penetration of the impacting atoms means all of the energy carried by the entire cluster ion is consequently dissipated in an extremely small volume in the top surface layer during a period on the order of $10^{-12}$ seconds (i.e. one picosecond). This is different from the case of ion implantation which is normally done with conventional monomer ions and where the intent is to penetrate into the material, sometimes penetrating several thousand angstroms, to produce changes in the surface properties of the material. Because of the high total energy of the cluster ion and extremely small interaction volume, the deposited energy density at the impact site is far greater than in the case of bombardment by conventional monomer ions.

Reference is now made to FIG. 1 of the drawings which shows the GCIB processor 100 of this invention utilized for applying or adhering drugs to the surface of a medical device such as, for example, coronary stent 10. Although not limited to the specific components described herein, the processor 100 is made up of a vacuum vessel 102 which is divided into three communicating chambers, a source chamber 104, an ionization/acceleration chamber 106, and a processing chamber 108 which includes therein a uniquely designed workpiece holder 150 capable of positioning the medical device for uniform GCIB bombardment and drug application by a gas cluster ion beam.

During the processing method of this invention, the three chambers are evacuated to suitable operating pressures by vacuum pumping systems 146a, 146b, and 146c, respectively. A condensable source gas 112 (for example argon or $N_2$) stored in a cylinder 111 is admitted under pressure through gas metering valve 113 and gas feed tube 114 into stagnation chamber 116 and is ejected into the substantially lower pressure vacuum through a properly shaped nozzle 110, resulting in a supersonic gas jet 118. Cooling, which results from the expansion in the jet, causes a portion of the gas jet 118 to condense into clusters, each consisting of from several to several thousand weakly bound atoms or molecules. A gas skimmer aperture 120 partially separates the gas molecules that have not condensed into a cluster jet from the cluster jet so as to minimize pressure in the downstream regions where such higher pressures would be detrimental (e.g., ionizer 122, high voltage electrodes 126, and process chamber 108). Suitable condensable source gases 112 include, but are not necessarily limited to, argon, nitrogen, carbon dioxide, oxygen.

After the supersonic gas jet 118 containing gas clusters has been formed, the clusters are ionized in an ionizer 122, The ionizer 122 is typically an electron impact ionizer that produces thermo-electrons from one or more incandescent filaments 124 and accelerates and directs the electrons causing them to collide with the gas clusters in the gas jet 118, where the jet passes through the ionizer 122. The electron impact ejects electrons from the clusters, causing a portion the clusters to become positively ionized. A set of suitably biased high voltage electrodes 126 extracts the cluster ions from the ionizer 122, forming a beam, then accelerates the cluster ions to a desired energy (typically from 1 keV to several tens of keV) and focuses them to form a GCIB 128 having an initial trajectory 154. Filament power supply 136 provides voltage $V_F$ to heat the ionizer filament 124. Anode power supply 134 provides voltage $V_A$ to accelerate thermoelectrons emitted from filament 124 to cause them to bombard the cluster containing gas jet 118 to produce ions. Extraction power supply 138 provides voltage $V_E$ to bias a high voltage electrode to extract ions from the ionizing region of ionizer 122 and to form a GCS 128. Accelerator power supply 140 provides voltage $V_{Acc}$ to bias a high voltage electrode with respect to the ionizer 122 so as to result in a total GCIB acceleration energy equal to $V_{Acc}$, electron volts (eV). One or more lens power supplies (142 and 144, for example) may be provided to bias high voltage electrodes with potentials ($V_{L1}$ and $V_{L2}$ for example) to focus the GCIB 128.

A medical device, such as coronary stent 10, to be processed by the GCIB processor 100 is held on a workpiece holder 150, and disposed in the path of the GCIB 128 for irradiation. The present invention may be utilized with medical devices composed of a variety of materials, such as metal, ceramic, polymer, or combinations thereof. In order for the stent to be uniformly processed using GCM, the workpiece holder 150 is designed in a manner set forth below to manipulate the stent 10 in a specific way.

Figure 2:
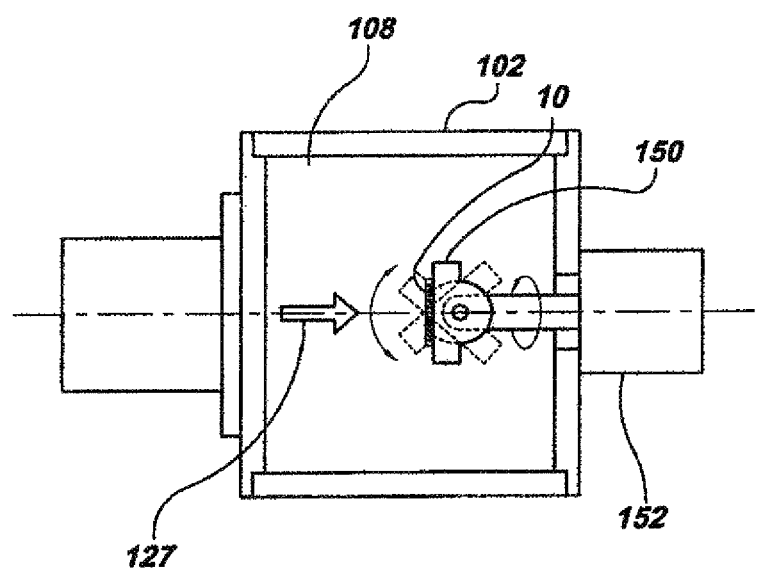
FIG. 2 is an exploded view of a portion of the gas cluster ion beam processing system of FIG. 1 showing the workpiece holder.

Referring now to FIG. 2 of the drawings, medical device surfaces that are non-planar, such as those of stents, must remain oriented within a specific angle tolerance with respect to the normal beam incidence to obtain paramount effect to the stent surfaces utilizing GCIB. This requires a fixture or workpiece holder 150 with the ability to be fully articulated to orient all non-planar surfaces of stent 10 to be modified within that specific angle tolerance at a constant exposure level for process optimization and uniformity. Any stent 10 containing surfaces that would be exposed to the process beam at angles of greater than +/−15 degrees from normal incidence may require manipulation. More specifically, when applying GCIB to a coronary stent 10, the workpiece holder 150 is rotated and articulated by a mechanism 152 located at the end of the GCIB processor 100. The articulation/rotation mechanism 152 preferably permits 360 degrees of device rotation about longitudinal axis 154 and sufficient device articulation about an axis 156 perpendicular to axis 154 to maintain the stent's surface to within +/−15 degrees from normal beam incidence.

Referring back to FIG. 1, under certain conditions, depending upon the size of the coronary stent 10, a scanning system may be desirable to produce uniform smoothness. Although not necessary for GCIB processing, two pairs of orthogonally oriented electrostatic scan plates 130 and 132 may be utilized to produce a raster or other scanning pattern over an extended processing area. When such beam scanning is performed, a scan generator 156 provides X-axis and Y-axis scanning signal voltages to the pairs of scan plates 130 and 132 through lead pairs 158 and 160 respectively. The scanning signal voltages are commonly triangular waves of different frequencies that cause the GCIB 128 to be converted into a scanned GCIB 148, which scans the entire surface of the stent 10. Additional means for orienting, articulating and/or rotating devices such as stents and orthopedic products are disclosed in U.S. Pat. No. 6,491,800 to Kirkpatrick, et al., U.S. Pat. No. 6,676,989 to Kirkpatrick, et al., and U.S. Pat. No. 6,863,786 to Blinn, et al., the contents of each which are hereby incorporated by reference.

When beam scanning over an extended region is not desired, processing is generally confined to a region that is defined by the diameter of the beam. The diameter of the beam at the stent's surface can be set by selecting the voltages ($V_{L1}$ and/or $V_{L2}$) of one or more lens power supplies (142 and 144 shown for example) to provide the desired beam diameter at the workpiece.

In one processing step related to the present invention, the surface of a medical device is irradiated with a GCIB prior to the deposition of any substance on the surface thereof. This will remove any contaminants and oxide layers from the stent surface rendering the surface electrically active and capable of attracting and bonding drug and polymer molecules that are then introduced to the surface.

Figure 3:
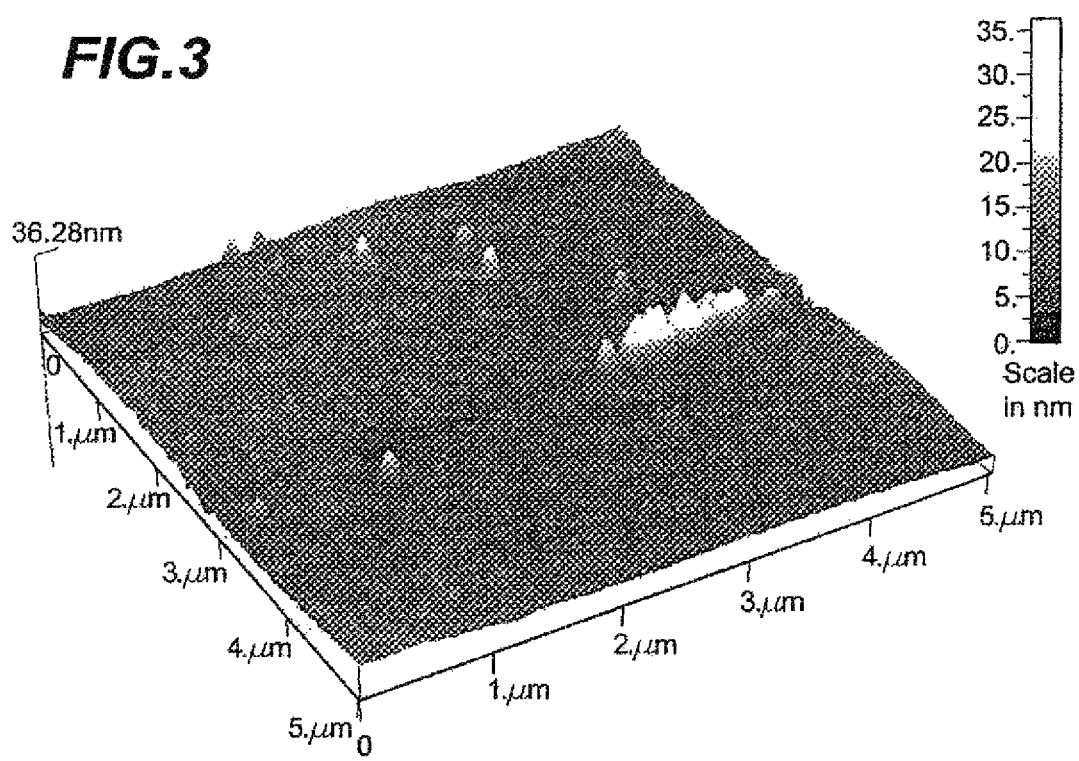
FIG. 3 is an atomic force microscope image showing the surface of a coronary stent before GCIB processing.
Figure 4:
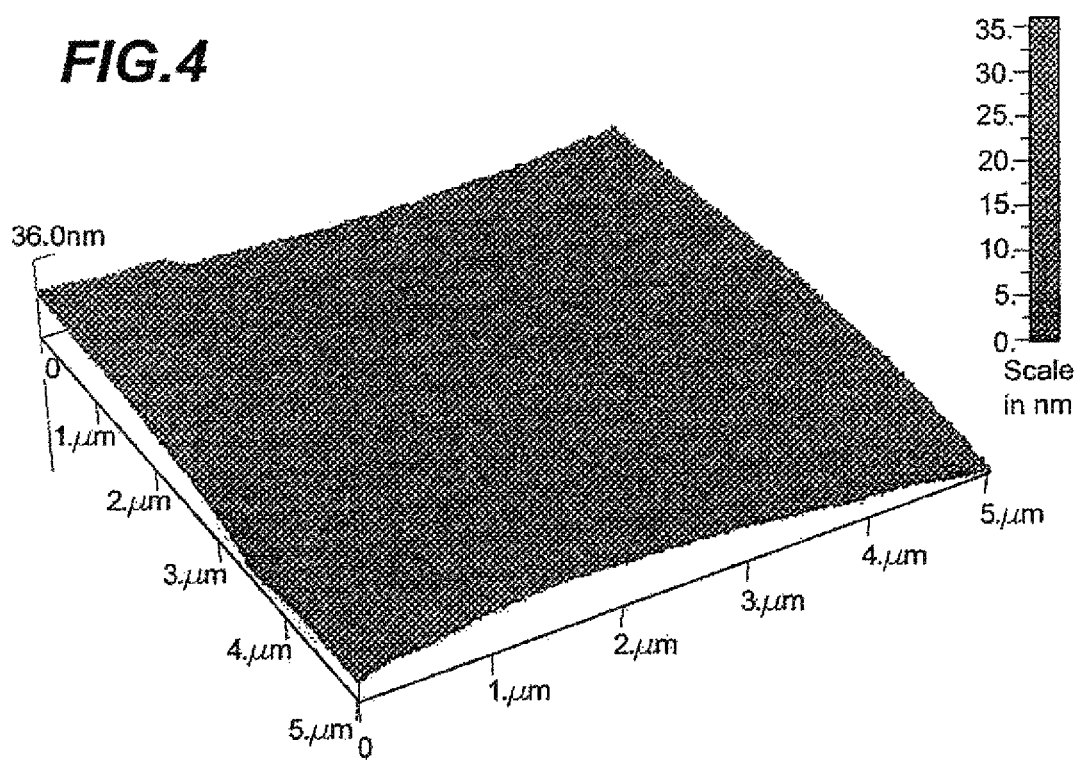
FIG. 4 is an atomic force microscope image showing the surface of a coronary stent after GCIB processing.

As the atomic force microscope (AFM) images shown in FIGS. 3 and 4 demonstrate, it is possible to dramatically affect the medical device surface utilizing gas cluster ion beam processing. FIG. 3 shows a stent surface before GCIB treatment with gross surface micro-roughness on a strut edge. The surface roughness measured an $R_a$ of 113 angstroms and an $R_{RMS}$ of 148 angstroms. These irregularities highlight the surface condition at the cellular level where thrombosis begins. FIG. 4 shows the stent surface after GCIB processing where the surface micro-roughness has been eliminated without any measurable physical or structural change to the integrity of the stent itself. The post-GCIB surface roughness measured an $R_a$ of 19 angstroms and an $R_{RMS}$ of 25 angstroms. In this manner, GCIB processing also provides the added benefit of smoothing the surface of the medical device. Non-smooth surfaces may snare fibrinogen, platelets, and other matter further promoting stenosis.

Figure 5:
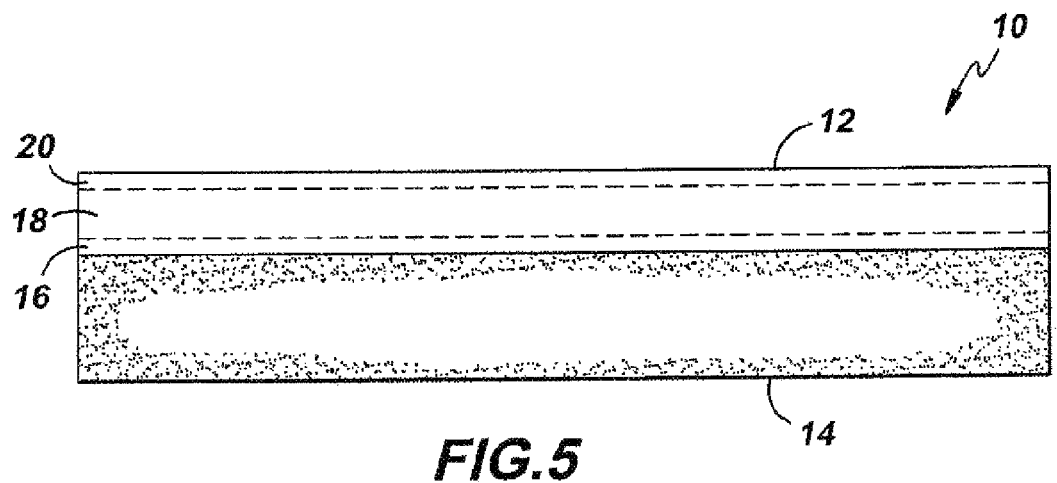
FIG. 5 is across section of a drug delivery system prior to processing in accordance with the present invention.

With reference to FIG. 5, a drug delivery system 10, which includes a drug containing medium 12 and an optional substrate or medical device 14, is shown prior to processing by the method of the present invention. Medical device 14 is only representational and may take any suitable form. Device 14 may include an implantable medical device such as a stent or any other medical device which may benefit from an in situ drug delivery mechanism. Optionally, the use of substrate or device 14 may be limited to the fabrication of drug containing medium 12, wherein substrate or device 14 is removed from medium 12 prior to implantation. Substrate or device 14 maybe he constructed of any suitable material such as, for example, metal, ceramic or a polymer. Portions of substrate or device 14 may also be surface treated using GCIB in accordance with the method mentioned above, prior to the application of drug/polymer medium 12.

Drug containing medium 12 may take any suitable form such as the various polymer arrangements discussed above. Medium 12 may include just a single layer of drug containing material, or it may include multiple layers 16, 18, 20, as described above. Although the existing art identifies the use of an outer layer to control initial drug release, the process of the present invention may be used with this known arrangement to further control surface characteristics of the medium, including the drug release rate after initial in situ liquid exposure. Drug medium 12 may be applied to device 14 in any suitable arrangement from just a portion to complete or almost complete enclosure of device 14.

One method of application of medium 12 to device 14 uses a drug polymer mixture with a volatile solvent, which is deposited upon a surface of device 14. The solvent is evaporated to leave a cohesive drug/polymer mixture in the form of medium 12, attached to the substrate. Once the solvent is evaporated, drug medium 12 may form a cohesive mixture or mass and thereby provide a suitable drug delivery system, even in the absence of device 14.

Figure 6:
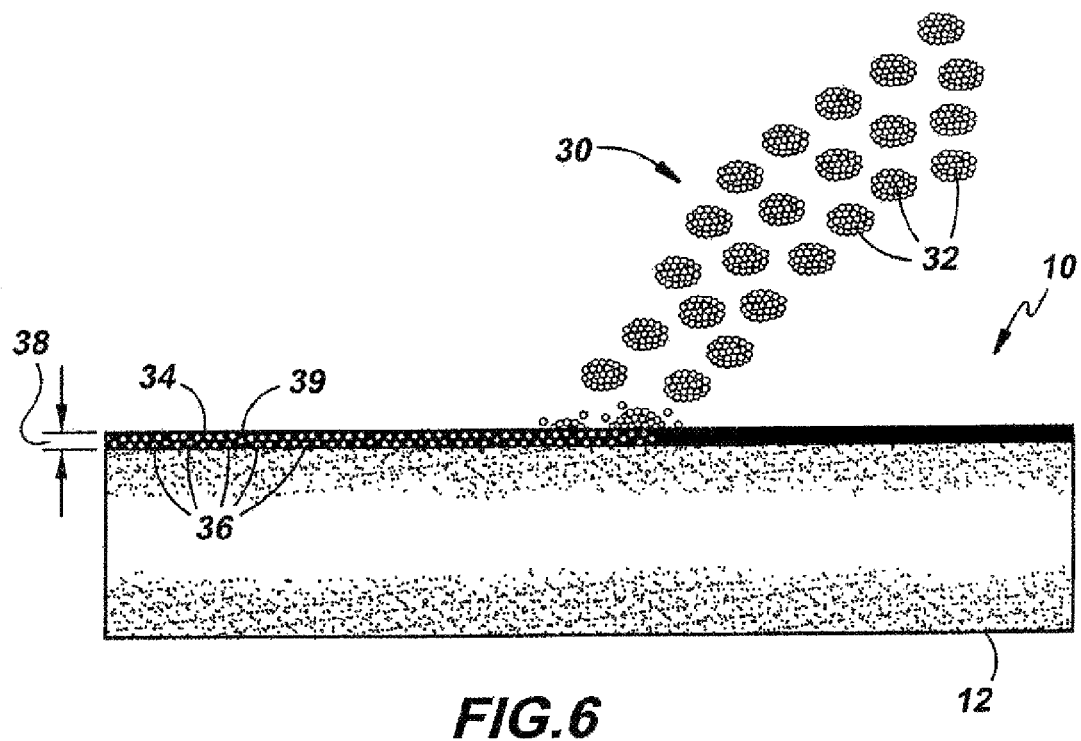
FIG. 6 is a cross section of the drug delivery system of FIG. 5 shown during gas cluster ion beam processing performed in accordance with the present invention.

With reference to FIG. 6, the drug delivery system 10 is shown undergoing irradiation with a gas cluster ion beam. A stream 30 of gas cluster molecules is being scanned across the cross section of drug delivery device 10. The clusters 32 break up upon impact with the surface 34 resulting in the shallow implantation of individual or small groups of molecules 36. Most of the individual molecules 36 stop within the first couple of molecular levels of medium 12 with the result that most of a thin layer 38 at surface 34 is densified or carbonized by the impinging molecules. The sealing of surface 34 is not complete, as various openings 39 remain in surface 34 which openings allow for the elution of drugs from medium 12. Thus, it is through the amount of GCIB irradiation that the characteristics of surface 34 are determined. The greater the amount of irradiation, the fewer and smaller are the openings in surface 34, thereby slowing the release of drugs from medium 12. Also, this densification or carbonization of surface 34 causes pacification or sealing of surface 34, which can decrease the bio-reactivity of surface 34 in contact with living tissue. In the case of some polymer materials which may be used for medium 12, the densification or carbonization can limit the release of volatile organic compounds by the medium 12 into surrounding living tissue. Thus, the process of the present invention enhances the choices of materials which may be used to construct medium 12 and can reduce risk factors associated with those material choices.

Studies have suggested that a wide variety of drugs may be useful at the site of contact between the medical device and the in situ environment. For example, drugs such as anti-coagulants, anti-prolifics, antibiotics, immune-suppressing agents, vasodilators, anti-thrombotic substances, anti-platelet substances, and cholesterol reducing agents may reduce instances of restenosis when diffused into the blood vessel wall after insertion of the stent. Although the present invention is described in reference to stents, its applications and the claims hereof are not limited to stents and may include any contact with a living body where drug delivery may be helpful.

Although the invention has been described with respect to various embodiments, it should be realized this invention is also capable of a wide variety of further and other embodiments within the spirit and scope of the appended claims.

The invention claimed is:

1. A method for producing a drug delivery system, comprising the steps of:
   providing a member including a combination of a drug substance and a polymer or other material; and
   forming a layer on a surface of the combination, which determines a release rate for the drug substance, including irradiation by gas cluster ion beam,
   wherein the layer is an encapsulating layer formed by densifying or carbonizing components of the combination of the drug substance and the polymer or the other material by the gas cluster ion beam irradiation.

2. The method of claim 1, further including a step of exposing the drug delivery system to an in-situ liquid by surgical implantation, and wherein the layer controls a drug release rate subsequent to the exposing.

3. The method of claim 1, wherein the member is a coronary stent.

4. The method of claim 1, wherein a surface of the drug delivery surface is a pacified surface.

* * * * *